United States Patent [19]

Flisram et al.

[11] Patent Number: 5,379,633
[45] Date of Patent: Jan. 10, 1995

[54] MEASUREMENT OF CUTTING EDGE SHARPNESS

[75] Inventors: Dennis G. Flisram, Madison; James A. Rattmann, Sun Prarie; Gary R. Skaar, Marshall; Terry L. Holmes, Monona, all of Wis.

[73] Assignee: Oscar Mayer Foods Corporation, Madison, Wis.

[21] Appl. No.: 65,091

[22] Filed: May 20, 1993

[51] Int. Cl.6 .................................. G01M 13/00
[52] U.S. Cl. ........................................... 73/104
[58] Field of Search ............ 73/104, 862.541, 862.542, 73/78, 81, 83

[56] References Cited

U.S. PATENT DOCUMENTS

| | | | |
|---|---|---|---|
| 4,178,797 | 12/1979 | Kozlowski, Jr. | 73/104 |
| 4,351,029 | 9/1982 | Maxey et al. | 73/104 |
| 5,119,512 | 6/1992 | Dunbar et al. | 2/167 |
| 5,181,416 | 1/1993 | Evans | 73/104 |

FOREIGN PATENT DOCUMENTS 533855 11/1976 U.S.S.R. ........................... 73/104

*Primary Examiner*—Robert Raevis
*Attorney, Agent, or Firm*—Lockwood, Alex, Fitzgibbon & Cummings

[57] ABSTRACT

An objective measurement of the relative sharpness of a slicing blade is made in accordance with the apparatus and method of this invention by making a test cut in a test specimen in a controlled manner in a sharpness tester device which records the peak force required to cut a standard test specimen 44.

19 Claims, 3 Drawing Sheets

U.S. Patent　　　Jan. 10, 1995　　　Sheet 1 of 3　　　5,379,633
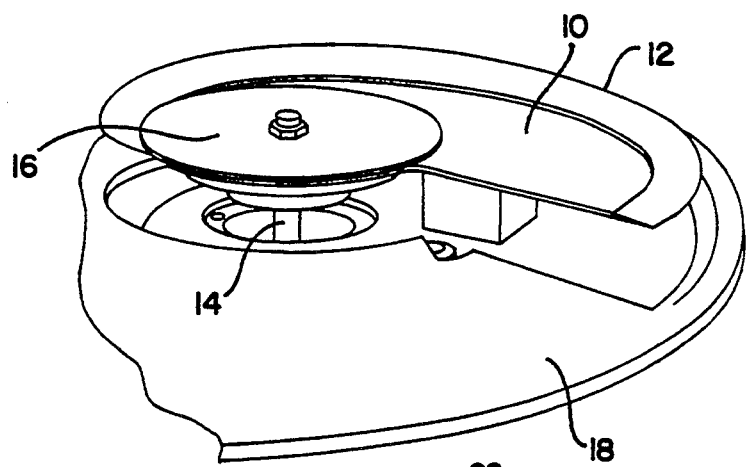
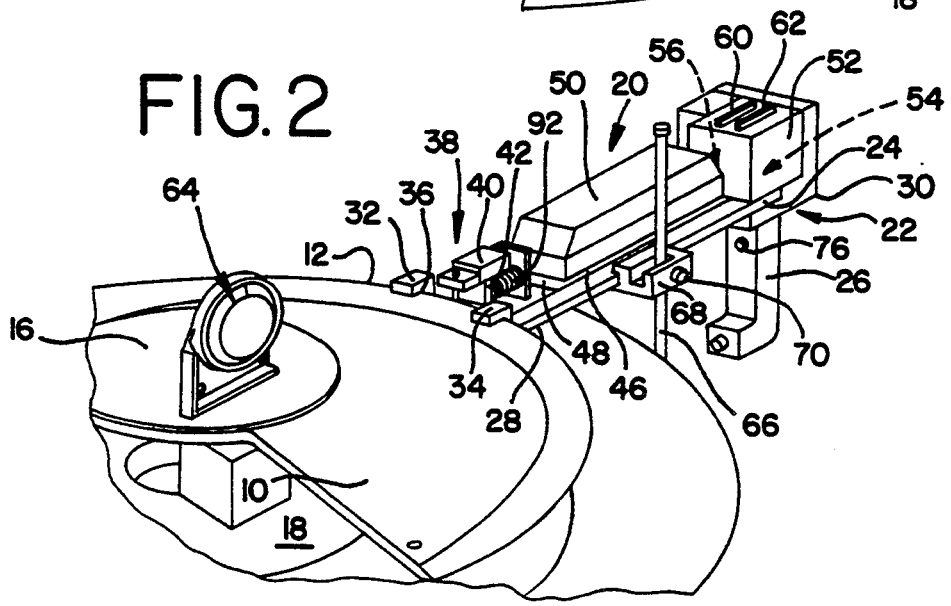
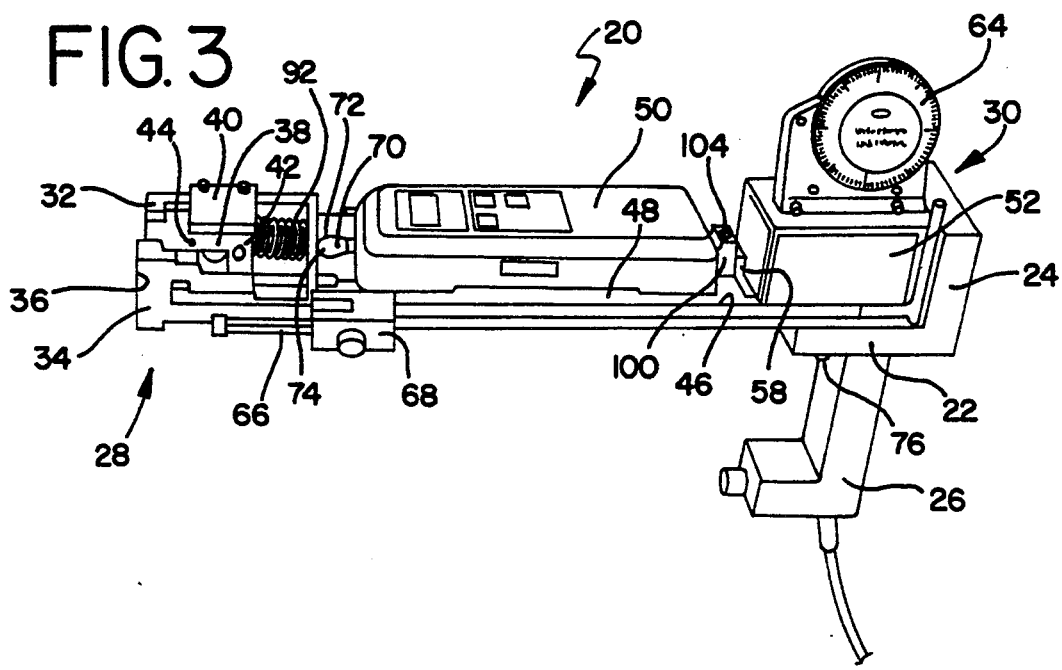

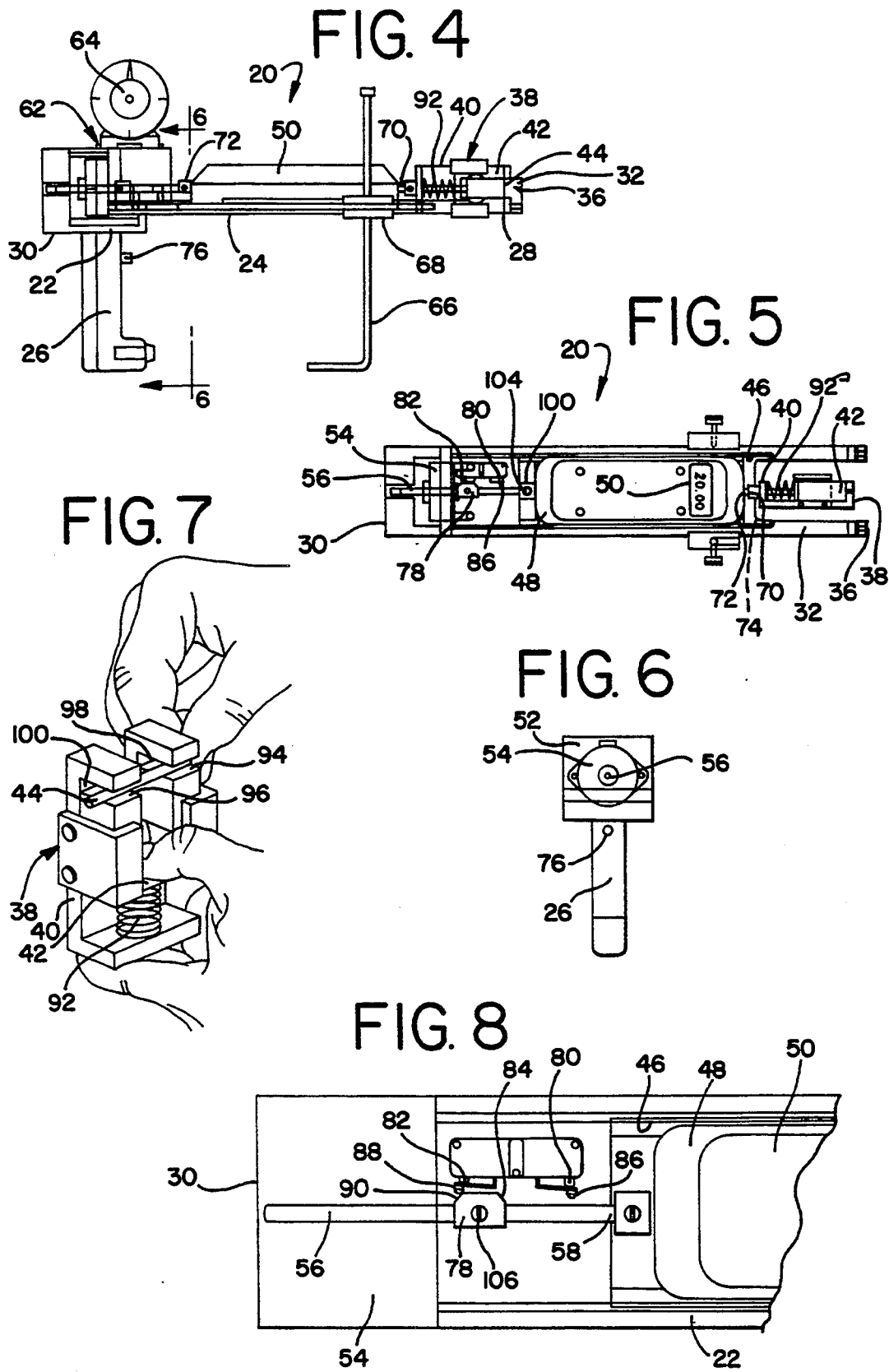

MEASUREMENT OF CUTTING EDGE SHARPNESS

BACKGROUND OF THE INVENTION

The present invention generally relates to devices and methods for determining the relative sharpness or dullness of a blade cutting edge. More particularly, it relates to a new and improved semi-automatic, hand-held apparatus for objectively measuring the relative sharpness of a slicing blade.

In the field of commercially prepared, pre-packaged sliced meats, carefully sliced stacks of meat products are prepared and packaged in an attractive manner for sale in a grocery store refrigeration case. Illustrative examples of these packaged sliced meat products include bologna, salami, ham, turkey and chicken. A great many of these food products are packaged in called see-through pedestal packages, wherein substantially uniform slices, having smooth substantially perfect edges and surfaces, are generally pressed into a raised bubble or blister package portion wherein they may be readily viewed by the purchaser. In these packages, near perfection in slice quality and stacking is prerequisite to successful sales.

Blade sharpness effects both slice and stack quality. Dull blade cutting edges are responsible for a number of identified defects in the sliced meat products such as tails, blown edges, torn slices, ragged edges, folded slices, skewed stacks, fluffed stacks and accordion stacks.

In the commercial high speed, high volume meat packaging processes, the above-identified problems caused by a dull blade in the automatic slicing machines and operations are extremely time consuming and expensive. Re-forming or re-aligning the stacks by hand increases the labor cost associated with the packaging. Irregular stacking, and especially the production of irregular slices increases the amount of food waste which is very expensive to providers.

Heretofore, the methods for evaluating the slicer blade sharpness have relied upon subjective evaluations such as, running a thumb over the edge of a blade or getting the feel of the blade by making a manual test slice of a meat material. Differences in moisture and other properties of the meat being sliced may require different degrees of sharpness to provide problem-free slices in uniform stacks in the automatic slicing equipment. A subjective determination that a blade is sharp from one kind of meat may be inaccurate and inappropriate for another grade of meat requiring a different sharpness level.

Accordingly, to overcome the shortcomings of prior art subjective methods, it is an object of the present invention to provide a hand-held test instrument which is effective to take the guess work out of evaluating slicer blade sharpness.

It is another object of the present invention to provide a new and improved device capable of objectively measuring the relative sharpness of the cutting edge of a blade which is capable of creating objective sharpness standards for blades which may be correlated to different types of meat products to be sliced on given different slicer brands or models.

It is a further object of the present invention to provide a new and improved blade sharpness measuring device and method whose results exhibit little or no operator bias.

It is still another object of the present invention to provide a new and improved blade sharpness measuring device whose sharpness determinations are substantially consistent at room temperatures of between about 40° F. and 75° F.

It is a further object of the present invention to provide a new and improved sharpness measuring device to permit a blade to be tested for requisite sharpness before a slicing operation has begun to effectively reduce or eliminate food waste associated with imperfect slicing and stacking heretofore caused by dull blades.

SUMMARY OF THE INVENTION

In accordance with these and other objects, the present invention provides a new and improved apparatus for objectively measuring the relative sharpness of a slicer blade. The apparatus in accordance with this invention comprises a sample holder for positioning at least a portion of a test specimen or test sample in a given position by applying tension to that portion of the test sample or to the opposed ends of the test sample. The apparatus further includes means for reciprocably advancing the sample holder toward and away from a cutting edge portion of the slicer blade whose relative sharpness is being determined. The reciprocable advancing means is operable to advance the sample holder between a first position wherein the test sample is spaced a first distance away from the cutting edge of the blade and a second position wherein the cutting edge extends beyond the given position of the test sample, such that any test sample positioned in said sample holder is first contacted and thereafter cut through by the cutting edge of the blade as said sample holder is advanced from the first position to the second position. The apparatus also includes means for quantitatively determining a maximum force needed to continuously advance the test sample mounted in said sample holder from said first position to said second position.

In accordance with an alternate aspect of the present invention, the relative sharpness of a slicing blade is objectively determined by contacting the cutting edge of the slicer blade with a test specimen having known physical properties in a hand held device which reproducibly advances the test specimen toward the blade under test. Objective determinations of the force required to obtain cut-through of the test specimen employing the advancing mechanism are recorded and correlate to the relative sharpness or dullness of the cutting edge being contacted by the test specimen with the device.

In accordance with the preferred embodiment, the sample holder includes a spring loaded clamping mechanism for holding an elongate cylindrical or string-shaped test media specimen in a taut, tensioned position by gripping the opposed ends of the test sample. The sample holder is connected to a force gauge, which is in turn connected to the actuator rod of a linear actuator, operative to advance the sample holder toward the cutting edge of the blade at a constant and continuous advancing rate. The stroke length of the linear actuator in both a forward and rearward direction, toward and away from the cutting edge, respectively, is preferably limited to a relatively short predetermined stroke length. Also in accordance with the preferred embodiment, the measurement device is mounted on a hand held gun body which includes a blade rest for generally locating the apparatus with respect to the blade for measurement, appropriate supporting legs for holding the gun in a fixed position during measurement, means for maintaining the angle of the measurement at an appropriate angle to the blade, and a handle with a trigger actuator for actuating the measurement test once the blade tester has been arranged and located in an appropriate measurement position.

The new and improved objective sharpness measuring apparatus and method of this invention takes the guesswork out of evaluating slicer blade sharpness. The new and improved apparatus in accordance with this invention accurately and consistently determines whether a blade is sharp enough to make quality slices under production conditions. The hand held measurement gun device eliminates the need to use unreliable tests of sharpness heretofore employed, such as running a thumb over the edge of a blade, which are inaccurate and extremely subjective at best. Statistical studies have verified the reproducibility of the measurements made with the device and the statistical significance of the relative sharpness values in pounds now determined with the device correlate well to objective evidence of blade sharpness as expressed in slicing and stacking uniformity of food products.

Other objects and advantages of the present invention will become apparent from the following Detailed Description, taken in conjunction with the Drawings, in which:

BRIEF DESCRIPTION OF THE DRAWINGS

FIG. 1 is a perspective view of an automatic slicer and slicing blade, with the blade shown in a raised position relative to the slicer surface;

FIG. 2 is a perspective view of the new and improved blade sharpness tester of the present invention shown in use, measuring the sharpness of a portion of the cutting edge of the raised slicer blade shown in FIG. 1;

FIG. 3 is a perspective view of the new and improved sharpness tester device in accordance with a preferred embodiment of this invention;

FIG. 4 is a side elevation view of the new and improved sharpness tester apparatus of the present invention;

FIG. 5 is top plan view of the new and improved sharpness tester apparatus shown in FIG. 4;

FIG. 6 is a front elevation view of the new and improved sharpness tester device taken along view line 6—6 in FIG. 4, with portions of the support leg and angle finder removed for clarity;

FIG. 7 is an enlarged perspective view of the sample holder for holding a test sample under tension in accordance with the new and improved sharpness tester of the present invention:

FIG. 8 is an enlarged fragmentary top plan view of the new and improved actuator rod stroke length control for limiting the movement of the test specimen in either direction during sharpness testing;

DETAILED DESCRIPTION OF THE PREFERRED EMBODIMENT

Figure 9:
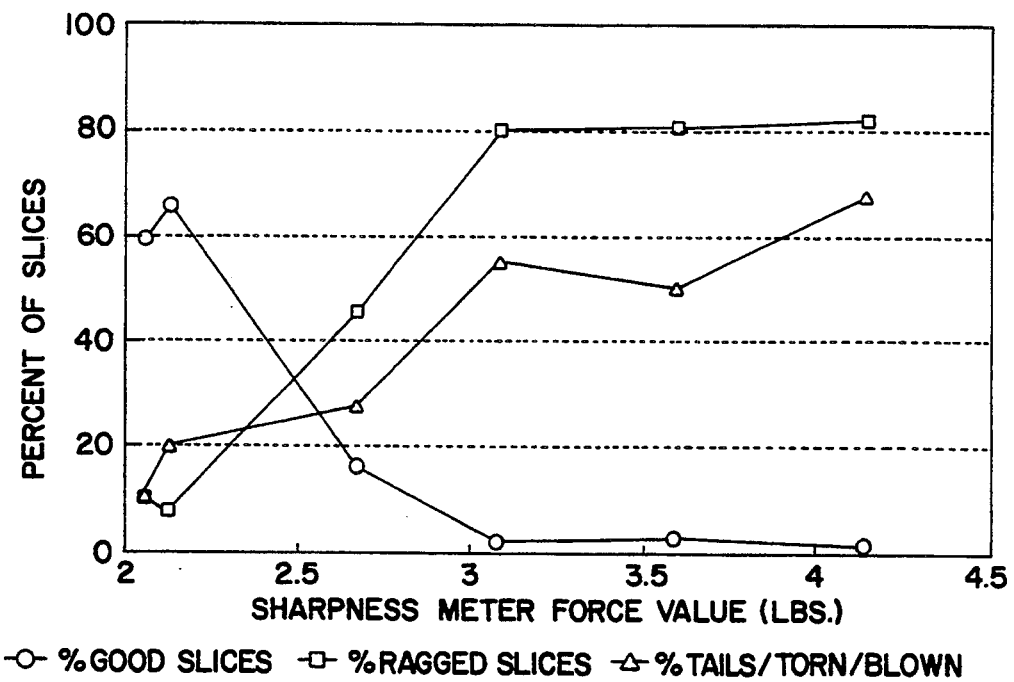
FIG. 9 is a graphical plot illustrating that as the maximum cut-through force measured by the new and improved sharpness tester device of this invention increases, the percentage of low quality of slices obtained with that blade is also observed to increase.

Referring now to FIG. 1, an illustrative commercial slicing blade 10 having a curved cutting edge 12, is shown. Slicing blade 10 is mounted to a rotating drive shaft 14 at its center hub portion 16. As shown in FIG. 1, slicing blade 10 has been raised or elevated relative to the surrounding slicing deck surface 18 in order to expose the slicing blade and its cutting edge 12 to permit objective measurement of the relative sharpness of the cutting edge 12.

Slicing blade 10 is illustrative of many commercial slicing blade configurations available on various models of commercial meat and food slicing equipment. Commercial sources of slicing blades and equipment of the type illustrated by the slicer shown in FIG. 1 include commercial slicers from Great Lakes Company, ANCO, Cashin, Formax, and Thurne slicers, to name but a few. The rotating slicer blades used in these devices may have a curved, eccentric, elliptical, circular, orbital, or even linear cutting edge configuration. Although the sharpness tester or meter of the present invention is especially suited for use on commercial slicing equipment, the apparatus, method and underlying theories of measurement in accordance with this invention, may also be applied to other blades having a cutting edge portion whose relative sharpness or dullness needs to be objectively determined from time to time.

Referring now to FIG. 2, the new and improved objective sharpness measurement apparatus in accordance with the preferred embodiment, generally referred to by reference numeral 20, is shown in an intended position of use measuring the sharpness of cutting edge 12 on the raised slicing blade 10. Sharpness measurement meter 20 generally includes a gun body 22 having an upper mounting portion 24 and a lower, dependent handle portion 26. The upper mounting portion 24 includes a front end 28 and an opposed rear end 30.

In accordance with the preferred embodiment depicted therein, sharpness tester 20 includes a pair of spaced apart blade holders or blade rests, 32 and 34, each having a blade receiving recess area or groove 36 for generally locating the front end 28 of the sharpness tester 20 and engaging it with respect to slicing blade 10. A sample holder subassembly 38 is disposed between the blade rest 32 and 34 and includes means for positioning an elongated test specimen or test sample in a given position in the sample holder 38 under tension. In the preferred embodiment shown in FIG. 2, sample holder subassembly 38 includes an outer clamp housing 40 and an inner spring loaded clamping member 42, for holding a predetermined length of a generally cylindrical rope-like test specimen 44 of a predetermined test media. As depicted in FIG. 2, sample holder subassembly 38 is adapted to hold the length of test media 44 under tension by gripping the opposed ends of test specimens 44 between the outer and inner clamp members 40 and 42, respectively, and so that the longitudinal axis of the test sample 44 is disposed at a generally perpendicular orientation with respect to the cutting edge 12.

Upper body portion 24 also includes an elongated slide-receiving recess portion 46 adapted to slidably receive a slide mounting block 48 therein. Slide mounting block 48 is reciprocably slidably mounted in slide receiving recess 46. In accordance with the preferred embodiment depicted in FIG. 2, a digital electronic force gauge 50 is fixedly mounted to slide block 48 for slidable, reciprocal movement therewith with respect to the gun body 22. The sample holder subassembly 38 is coupled to the front end of force gauge 50 and is adapted to be moved toward and away from cutting edge 12 by movement of the slide block 48 and force gauge 50.

As shown in FIG. 2, a rear cover or housing member 52 covers an inner linear actuator 54. The linear actuator 54 includes an actuator rod 56 having a front end 58 which is coupled to the rear end of the slide block 48. Linear actuator 54 is operative to reciprocably advance and retract the actuator rod 56 toward and away from the front end 28 and cutting edge 12 in a smooth, preferably constant, continuous advancing rate. Linear actuator 54 moves actuator rod 56, the slide block 48, the force gauge 50, and the sample holder 38 through a range of positions including: a first position wherein the sample holder 38 and its held and positioned test specimen 44 are spaced from the cutting edge 12; a second position wherein the test specimen 44 is advanced in a forward direction toward slicing blade 10 into physical contact with the cutting edge 12; and a third position wherein forward travel of the sample holder 38 has continued to a point wherein the cutting edge 12 has cut through the sample media of the test specimen 44 and the cutting edge 12 extends relatively inwardly of the sample holder 38 and the given position of the tensioned test sample 44 mounted within the sample holder 38. A pair of magnetic mounting strips 60 and 62 are shown on top of rear housing 52, which are provided to releasably mount removable angle finder 64. Angle finder 64 is shown in FIG. 3 in position on the apparatus rear housing 52 and in FIG. 2 in a position where it has been removed from the apparatus housing and positioned on slicing blade 10 to determine the angle of the blade 10 with respect to a preselected reference position. In use and after the angle of the slicing blade 10 has been determined, the angle finder 64 is subsequently be moved back to its magnetically mounted position onto the magnetic strips 60 and 62 in order to assist the operator in adjusting the angle of gun body 22 so that it is substantially co-planar with the slicing blade 10 prior to measurement i.e., both the slicing blade 10 and the apparatus 20 are oriented at the same angle as illustrated in FIG. 2 with respect to a preselected reference datum.

In the preferred embodiment shown in FIG. 2, sharpness tester 20 also preferably includes at least one generally L-shaped arm 66 rotatably, adjustably mounted to upper portal, ion 24 on opposed sides thereof by means of the adjustable arm mounting brackets 68. Arm 66 is rotatable within mounting bracket 68 and the height of the arm is adjustable by means of a thumb screw 70 to assist the operator in maintaining the proper measurement angle for the sharpness tester.

In greater detail, and referring now to FIGS. 3-6, the digital electronic force gauge 50 is mounted on slide block 48 for slicing reciprocal movement with respect to slide recess 46. The front end of force gauge 50 includes a projecting extender rod 70 having a threaded free end 72 which is adapted to removably receive a complimentary matably threaded coupling nut 74 mounted on the rear end of the sample holder subassembly 38 to permit subassembly 38 to be installed onto force gauge 50. The rear end of the slide block 48 includes a slide connector block 100 into which the front end of actuator 56 may be secured by means of a threaded tightening screw 104.

Force gauge 50 is preferably a digital electronic force gauge or meter which may be battery operated from a rechargeable battery pack for special convenience. The force gauge preferably is operable in a peak force measurement mode to detect the maximum force encountered by the advancing test specimen 44 against cutting edge 12. In accordance with the invention, during a test cut using the test media specimen 44 the sample holder 38 advances toward the blade 10 and moves the test sample 44 into the cutting edge 12. The test specimen 44 initially resists the cutting action of the cutting edge 12. The constant advance rate of the sample holder 38 is effective to apply an increasing force of the test specimen 44 against the cutting edge 12 and the force peaks, or reaches a maximum, immediately before the test sample 44 yields to the cutting action of the blade 10. The force gauge 50 should be able to detect and display the maximum force encountered during a forward advance stroke of the linear activator 54 and activator rod 56. An especially preferred force gauge for use herein is a Shimpo TM brand digital force gauge model DF-40. Other force gauges including electric, piezo-electric, hydraulic and mechanical means for determining the peak force level during a test cut may also be employed.

Referring now to FIGS. 4-6, the linear actuator 54 in accordance with the preferred embodiment is a synchronous linear actuator effective to move the actuator rod 56 forward and back at a substantially constant advancing rate by a discrete or predetermined stroke length effective cause a test cut to be made in a test sample 44 positioned in the sample holder 38. A preferred linear actuator for use herein is a Hurst TM brand activator Model SL4013-001. Other linear actuators, such as air cylinder actuators or stepper motor actuators may also be used. The linear actuator 54 is operative upon squeezing a trigger control 76 located on handle portion 26 to cause the actuator to move in a forward direction at a constant rate. The rate may vary, however, a satisfactory advancing rate is between about 1/16 inch to about 1 inch per second, preferably between about ⅛ inch to about ½ inch per second. Release of the trigger 76 causes the actuator to move in a reverse retracting direction.

In accordance with the preferred embodiment, and as is best shown in FIGS. 4, 5, and 8, the forward and rearward limits of the actuator stroke length are preferably controlled by the operation of a cam block 78 mounted on actuator rod 56 (by way of a setscrew 106). During operation of the apparatus 20, as the linear actuator 54 moves the actuator rod 56 in either direction, its movement will cause the cam block 78 to contact either of the forward limit switch 80 or rearward limit switch 82. Upon squeezing and holding the trigger 76, actuator rod 56 moves forwardly, i.e., rightwardly as shown in FIG. 8, until the angled cam surface 84 on cam block 78 engages and deflects resilient cam arm follower 86, upwardly as shown, to activate the forward limit switch and halt further forward travel of the actuator rod 56. Release of the trigger 76 causes linear actuator 50 to retract the actuator rod 56 in a reverse leftward direction as shown in FIG. 8. At the end of the reverse stroke, the cam arm 88 on reverse limit switch 82 is contacted by cam surface 90 on cam block 78 which causes the cam arm 88 to be actuated upwardly as shown in FIG. 8 to activate the reverse stroke limit switch preventing further rearward travel of the actuator rod 56.

In accordance with the preferred embodiment best shown in FIGS. 4–5, blade rests 32 and 34 and recesses 36 extend forwardly on opposed sides of front end 28. The blade recess 36 is adapted to receive engage the cutting edge 12 portion of slicer blade 10 to generally locate the sharpness tester 20 against the slicer blade 10. As has been mentioned above, the use of the angle finder 64 assists in removing errors introduced by angular components being added to the measurement by assisting the operator in holding the sharpness tester 20 in a coplanar, head-on, blade-aligned position for measurement wherein the apparatus 20 and block 10 are maintained at the same angle.

In accordance with the present invention, a test sample is selected of a cylindrical length or rope of a tough synthetic rubbery material, which responds generally consistently when tensioned and clamped in the sample holder 38. As is best shown in FIG. 7, the preferred sample holder subassembly 38 includes an outer clamp housing 40 adapted to receive an inner clamping insert member 42. Inner clamp 42 is preferably spring biased by means of coil spring 92. The inner clamp 42 has a pair of spaced apart bearing surfaces 94 and 96 adapted to squeezably retain the opposed ends of test specimen 44 against complimentary clamping surfaces 98 and 100 on outer clamp 40. In an especially preferred embodiment, bearing surfaces 94 and 96 are provided with V-groove depressions (not shown) to receive and positively locate the test specimen 44 therein for clamping. Moreover, to further ensure that the test specimen 44 is held in linear tension along its length during the test cut procedure, downwardly projecting sample piercing spikes (not shown) may be provided in clamping surfaces 98 and 100 opposite the V-grooves to positively position and securely hold the test specimen for testing. As shown in FIG. 7, the inner clamp member 42 may be urged against the coil spring 92 to open the sample holder to remove previously cut test specimens and to re-load new test specimens in the sample holder for further testing. Although a solid rope-like test media specimen is preferred herein, hollow-tubes or washers may be used and only a portion of the test specimen needs to be held in tension at a test cut position in a sample holder.

In accordance with the apparatus and method of this invention, a test cut is made in a test specimen in a device which records the peak force required to cut the standard test specimen 44 in the standardized sharpness tester 20 for that particular slicing blade 10. The apparatus and method of this invention provides a relative blade sharpness value in pounds for that blade, which may thereafter be compared to the values determined for other blades to determine the sharpest blade of a group of blades tested or the measured value may be compared against a standardized scale determined for a slicer model and a particular meat to be sliced. For example, after a series of tests, it has been determined that satisfactory high quality slicing and stacking of a boiled ham meat product requires that the blade register a sharpness value using the blade tester 20 of this invention of less than or equal to 2.3 pounds. Thereafter, before commencing a commercial slicing operation for that meat product, the slicer blade of a commercial slicer may be tested using the sharpness tester 20 of this invention. If the tested value is above 2.3 pounds, the operator is thereby notified to sharpen the blade before commencing the slicing operation to prevent waste and corrective downtime.

Referring now to FIG. 9, a graph depicting the physical characteristics of slices made with a slicing blade having a sharpness meter force value in pounds as a function of percentage of slices sliced is shown. As shown in the graph the percentage of near-perfect, good, clean slices (read along the y-axis of the graph); starts to fall and the percentage of irregular slices starts to rise, as the detected sharpness value measured with the sharpness tester 20 goes up from about 2.25 to about 2.5 pounds (read along the x-axis of the graph).

Figure 10:
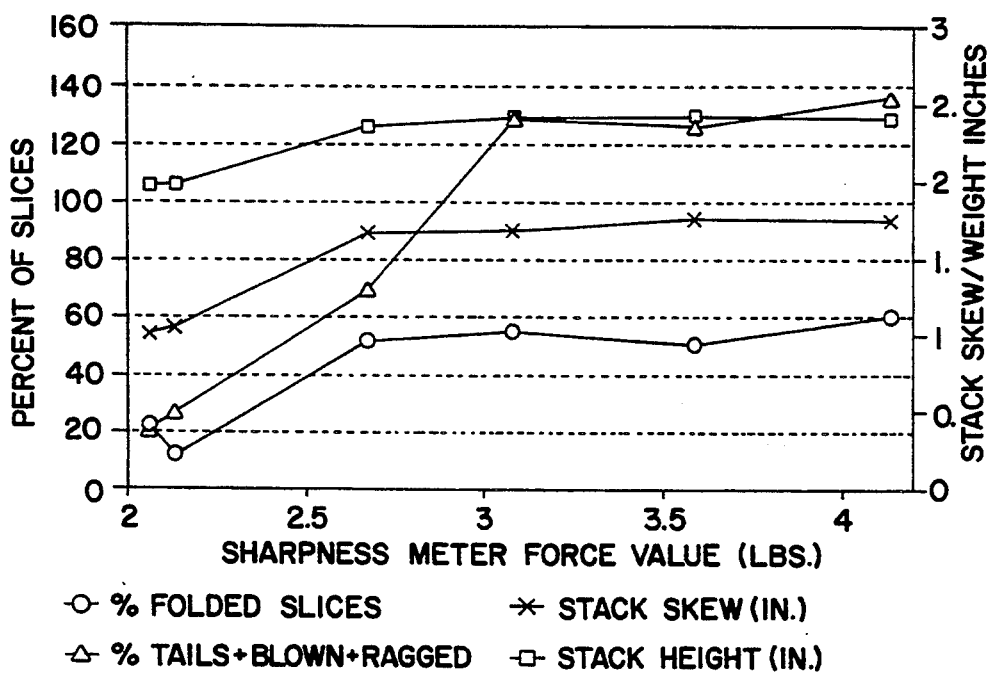
FIG. 10 is a graphical plot illustrating that as the maximum cut-through force measured by the new and improved sharpness tester device of this invention increases, the percentage of low quality of stacks of slices obtained with that blade is also observed to increase.

Referring to FIG. 10, a plot illustrating stacking quality and slicing quality as a function of measured blade sharpness in pounds is shown. This graph illustrates generally that as the measured blade sharpness increases using the sharpness tester 20 of this invention, problematic slices such as tails, blown edges and ragged edges were observed to increase and problematic stacking of slices such as stack skewing and folded slices also increased.

Further statistical studies employing regression, analysis-of-variance and contingency table chi-squared testing has revealed that the sharpness meter apparatus 20 is capable of correctly reporting relative blade sharpness with little or no operator bias. Accordingly, the device and method of the present invention provides an objective measurement of relative sharpness of a slicing blade to improve the quality and overall performance of commercial slicing operations.

Although the present invention has been described with reference to certain preferred embodiments, modifications or changes may be made therein by those skilled in this art. For example, alternative test specimen sample holder configurations may be employed. Instead of using a digital electronic force gauge, a piezoelectric or mechanical force gauge may be substituted. Furthermore, other linear actuators other than the preferred synchronous linear actuators may be used herein. All such obvious modifications and changes may be made herein by those skilled in this art without departing from the scope and spirit of this invention as defined in the appended claims.

We claim:

1. An apparatus for objectively measuring the relative sharpness of a food product slicer blade, the apparatus comprising:
   a sample holder for positioning at least a portion of a test sample in a given position and under tension;
   means for engaging said apparatus with respect to said slicer blade for measuring said slicer blade sharpness;
   means for determining both the angular disposition of said slicer blade and said apparatus with respect to a predetermined reference datum;
   means for matching and maintaining the angular disposition of the apparatus with the slicer blade angular disposition while said apparatus is in engagement with said slicer blade;
   means for advancing the sample holder toward a cutting edge portion of said slicer blade, wherein the test sample is initially contacted against the slicer blade cutting edge portion and is further advanced against said cutting edge portion until said slicer blade cutting edge cuts through said test sample; and
   means for quantitatively determining a maximum force associated with said slicer blade cutting through said test sample.

2. An apparatus as defined in claim 1, wherein said advancing means is capable of moving said sample holder through range of positions toward said slicer blade cutting edge consistently and reproducibly.

3. An apparatus as defined in claim 1, wherein said advancing means is manually operable and reciprocatable.

4. An apparatus as defined in claim 1, wherein said advancing means is automatically operable and reciprocatable.

5. An apparatus as defined in claim 1, wherein said advancing means includes a linear actuator for advancing said sample holder at a substantially constant forward rate and said force determining means is operatively connected to said sample holder.

6. An apparatus as defined in claim 1, wherein said sample holder includes clamping means adapted to apply tension to opposed ends of a test sample placed therein.

7. An apparatus as defined in claim 1, wherein said quantitative determination means includes a force gauge operatively connected to said sample holder.

8. An apparatus as defined in claim 7, wherein said force gauge is a digital electronic force gauge.

9. An apparatus as defined in claim 1, wherein said quantitative determination means is mounted for concerted movement with said sample holder intermediate the sample holder and said reciprocable advancing means.

10. An apparatus as defined in claim 1, wherein said angular disposition determining means further includes means for determining an appropriate angle for a path of travel of said sample holder in said apparatus so that the movement of said sample holder toward said slicer blade cutting edge is substantially co-planar with said slicing blade.

11. An apparatus as defined in claim 1, wherein said sample holder is reciprocatably mounted on said apparatus.

12. An apparatus as defined in claim 1, wherein said angular disposition means includes an angle measurement component detachably mounted on a housing portion of said apparatus.

13. An apparatus as defined in claim 1, wherein said apparatus includes an elongated body portion, a handle portion extending therefrom which permits an operator to hold said apparatus, the body portion terminating in said slicer blade engagement means, said slicer blade engagement means including at least one jaw member having a first recess which receives said slicer blade cutting edge, said apparatus body portion having a second recess disposed proximate to said jaw member and receiving said sample holder, said force determining means including an electrically powered force gauge.

14. An apparatus as defined in claim 1, wherein said apparatus supporting means includes an L-shaped support leg adjustably mounted to a body portion of said apparatus.

15. A handheld apparatus for measuring the sharpness of a food product slicing blade while the slicing blade is mounted in place on a slicing station, said slicing blade being disposed at an angular orientation to a preselected reference datum, the apparatus comprising:

a body portion, a handle portion extending from the body portion, a support member reciprocatably mounted on said body portion and adapted to be capable of movement on said apparatus back and forth along a longitudinal axis of said apparatus, the support member being adapted to retain a test media in place on said body portion in a manner so as to expose a portion of the test media in place on said body portion to a cutting edge of said slicing blade during operation of said apparatus, a force indicating member mounted on said body portion in operative connection with said support member and an actuator member for incrementally moving said support member toward and into contact with the slicing blade cutting edge during operation of said apparatus, whereby, the force indicating member indicates a maximum amount of force required by said slicing blade cutting edge to cut through said test media, said apparatus further including means for determining said slicing blade angular orientation of said slicing blade and of said apparatus body portion.

16. The sharpness measurement apparatus of claim 15, wherein said angular orientation determining means includes an angle finder member detachably mounted on said apparatus, whereby said angle finder member may be detached from said apparatus and applied to said slicing blade to determine said slicing blade angular orientation and returned to its position on said apparatus to enable an operator of said apparatus to orient said apparatus at said slicing blade angular orientation.

17. The sharpness measurement apparatus of claim 16, wherein said support member supports said test media on said apparatus in opposition to said slicing blade cutting edge.

18. The sharpness measurement apparatus of claim 15, wherein said body portion includes first and second members for engaging said slicing blade, the first engagement member including a frontal member of said body portion having at least one recess which receives said slicing blade therein, the second engagement member including an elongated rod member adjustably mounted to said body portion, the rod member having a leg which assists an operator of said apparatus in maintaining said apparatus body portion at said slicing blade angular orientation.

19. A handheld apparatus for measuring the sharpness of a food product slicing blade while the slicing blade is mounted in place on a slicing station, said slicing blade being disposed at an angular orientation to a preselected reference datum, the apparatus comprising:

a body portion, a handle portion extending from the body portion, a support member mounted on said body portion and capable of movement on said apparatus body portion along a longitudinal axis of said apparatus, the support member retaining a test media in place on said body portion in a manner to thereby expose a portion of the test media to a cutting edge of said slicing blade during operation of said apparatus, a force-indicating member mounted on said body portion in operative connection with said support member and an actuator member for incrementally moving said support member toward and into contact with the slicing blade cutting edge during operation of said apparatus, whereby, the force-indicating member indicates a maximum amount of force required by said slicing blade cutting edge to cut through said test media, said apparatus further including means for determining said slicing blade angular orientation in the form of an angle finder member detachably mounted on said apparatus body portion, whereby said angle finder member may be detached from said apparatus and applied to said slicing blade to determine said slicing blade angular orientation and subsequently returned to its position on said apparatus to enable our operator of said apparatus to orient said apparatus at said slicing blade angular orientation, said apparatus also further including first and second members for engaging said slicing blade, the first member extending from an end of said body portion and including a recess to receive said slicing blade therein, the second member including an elongated rod member adjustably mounted to said body portion, the rod member having a leg which assists the operator of said apparatus in maintaining said apparatus at said slicing blade angular orientation.

* * * * *